(12) United States Patent
Schirrmacher et al.

(10) Patent No.: US 8,142,791 B2
(45) Date of Patent: Mar. 27, 2012

(54) MULTI-MODAL CANCER THERAPY USING VIRAL HITCH-HIKING

(75) Inventors: Volker Schirrmacher, Heidelberg (DE); Philipp Beckhove, Heidelberg (DE); Philippe Fournier, Edingen (DE); Maximilian Aigner, Germering (DE)

(73) Assignee: Deutsches Krebsforschungszentrum Stiftung Des Offentlichen Rechts, Heidelberg (DE)

( * ) Notice: Subject to any disclaimer, the term of this patent is extended or adjusted under 35 U.S.C. 154(b) by 0 days.

(21) Appl. No.: 12/516,530

(22) PCT Filed: Nov. 23, 2007

(86) PCT No.: PCT/EP2007/062761
§ 371 (c)(1),
(2), (4) Date: May 27, 2009

(87) PCT Pub. No.: WO2008/065053
PCT Pub. Date: Jun. 5, 2008

(65) Prior Publication Data
US 2010/0062007 A1 Mar. 11, 2010

Related U.S. Application Data

(60) Provisional application No. 60/867,352, filed on Nov. 27, 2006.

(51) Int. Cl.
*C07K 16/46* (2006.01)
*C07K 14/55* (2006.01)
*C07K 16/08* (2006.01)
*A61K 38/20* (2006.01)

(52) U.S. Cl. .......... 424/192.1; 424/85.2; 424/134.1; 424/135.1; 424/136.1; 424/143.1; 424/146.1; 424/147.1; 424/214.1; 530/387.3; 530/388.26; 530/388.3

(58) Field of Classification Search .......... None
See application file for complete search history.

(56) References Cited

U.S. PATENT DOCUMENTS
6,180,370 B1 * 1/2001 Queen et al. .......... 435/69.6

FOREIGN PATENT DOCUMENTS
EP 1-275-724 A 1/2003

OTHER PUBLICATIONS

Lederman et al, Molecular Immunology 28:1171-1181, 1991.*
Henry et al, Cancer Res. 64: 7995-8001, Nov. 1, 2004.*
Stancoviski et al, Proceedings of the National Academy of Science USA 88: 8691-8695, 1991.*
Witte et al, Cancer and Metastasis Reviews 17: 155-161, 1998.*
Riemer et al, Mol. Immunol. 42: 1121-1124, 2005.*
Csatary, 1999, Anticancer Res 19 (1B)): 635-8.
Emergency Preparedness Information eXchange: Foreign Animal Diseases: Newcaste Disease. Burnaby, Canada. Telematics Research Lab, Simon Fraser University, 2002.
Csatary, 1993, Cancer Detect Prev 17(6): 619-27.
Kenney, 1994, J Natl Cancer Inst 86(16): 1185-6.
Kirn, 1996, Mol Med Today 2(12): 519-27.
Lorence, 1994, J Natl Cancer Inst 86(16): 1228-33.
Lorence, 1994, Cancer Res 54(23): 6017-6021.
Batliwalla, 1998, Mol Med 4(12): 783-94.
Reichard, 1992, J Surg Res 52(5): 448-53.
Schirrmacher, 1998, Semin Oncol 25(6): 677-96.
Moss, 1996, J Naturopathic Med 6(1): 23-32.
Nagai Y, Kato A, 1999, Microbiol. Immunol. 43: 613-624.
Scheid A, Choppin PW, 1977, Virology 80, 54-66.
Römer-Oberdörfer A et al., 2003, J. Gen. Virol. 84; 3121-3129.
Pecora AL et al., 2002, J. Clin. Oncol. 20, 2251-2266.
Schirrmacher V et al., 1999, Gene Ther. 6, 63-73.
Schirrmacher V, 2005, Cancer Immunol. Immunother. 54, 587-598.
Cole, 2005, Nature Med 11(10): 1073-1081.
Rooney, 2005, Nature Med 11(10): 1051-1052.
Thorne, 2006, Science 311: 1780-1784.
Schirrmacher, 2001, Int J Oncol 18: 945-952.
Gotoh, 1988, Virology 163(1): 174-182.
Pritzer, 1990, Virus Res 15(3): 237-242.
Haas, 2005, Vaccine 23: 2439-2453.
Haas, 2006, Int. J. Cancer, 118(3): 658-67.
Bonasio, 2006, Curr Opin Immunol, Aug., 18(4): 503-11.
Dela Cruz, 2004, Clin Exp Med 4(2): 57-64.
Köhler and Milstein, Nature 256, 1975, 495.
Galfré, Meth. Enzymol. 73, 1981, 3.
Conzelmann, 1998, Annu Rev Genet 32: 123-62.
Roberts, 1998, Virology 20, 247(1): 1-6.
Damle et al., 1981, PNAS, 5096-5098.

* cited by examiner

*Primary Examiner* — Phuong Huynh
(74) *Attorney, Agent, or Firm* — Birch, Stewart, Kolasch & Birch, LLP

(57) ABSTRACT

The present invention relates to an antibody fusion protein which specifically recognizes the VA, HN or F surface antigen of the New Castle Disease Virus (NDV), a surface molecule of a tumor-unspecific T cell or a surface molecule of a dendritic cell and an immunocytokine. Also encompassed by the present invention are polynucleotides encoding the aforementioned antibody fusion protein as well as tumor-unspecific key cells or dendritic cells bound by the antibody fusion protein. Moreover, the present invention relates to a method of treating a tumor in a subject comprising administering to the said subject the antibody fusion protein, the tumor-unspecific T cell, the dendritic cell or the polynucleotide of the invention. Preferably, the said tumor is a solid tumor.

2 Claims, 7 Drawing Sheets

(c)

MULTI-MODAL CANCER THERAPY USING VIRAL HITCH-HIKING

CROSS-REFERENCE TO RELATED APPLICATIONS

The present application is a National Stage entry of PCT/EP2007/062761, filed Nov. 23, 2007, which claims the benefit under 35 U.S.C. 119(3) of U.S. Provisional Application No. 60/867,352, filed Nov. 27, 2006. All of the applications listed above are hereby incorporated by reference in their entireties.

BACKGROUND OF THE INVENTION

The present invention relates to a multi-specific antibody fusion protein which specifically recognizes the viral antigens (VA) HN or F surface antigen of the Newcastle Disease Virus (NDV), a surface molecule of a tumor-unspecific T cell, or a surface molecule of a dendritic cell and an immunocytokine. Also encompassed by the present invention are polynucleotides encoding the aforementioned antibody fusion protein as well as tumor-unspecific T cells or dendritic cells bound by the antibody fusion protein. Moreover, the present invention relates to a method of treating a tumor in a subject comprising administering to the said subject the antibody fusion protein, the tumor-unspecific T cell, the dendritic cell or the polynucleotide of the invention. Preferably, the said tumor is a solid tumor.

Various current cancer therapies aim to target specific compounds to the tumor cells. The targeted compounds may be cytotoxic compounds or compounds which serve as marker molecules for the immune system triggering an immune response against the tumor. In some cases linker molecules such as bispecific antibodies have been used for tumor-targeting. Such bispecific antibodies, usually, recognize a tumor-specific surface molecule and the compound or cell to be targeted to the tumor cell. Cells which have been successfully brought into contact to the tumor cells by the aforementioned targeting approaches are for example tumor-specific T cells, i.e. T cells recognizing a tumor antigen. It is envisaged that these tumor-specific T cells elicit an immune response against the tumor whereby the tumor cells are killed. More recent approaches aim to even enhance said effects of T cell targeting by using tumor-specific T cells which have been loaded by oncolytic viruses.

An interesting candidate virus to be used in human therapy of cancer is NDV. NDV is a member of the paramyxoviridae family. Virulent strains elicit avian pest in various bird species. In humans, the virus is, usually, not harmful and elicits, at most, weak inflammatory responses such as conjunctivitis or laryngitis (Csatary, 1999, Anticancer Res 19 (1B):635-8; Emergency Preparedness Information eXchange: Foreign Animal Diseases: Newcastle Disease. Burnaby, Canada: Telematics Research Lab, Simon Fraser University, 2002; Csatary, 1993, Cancer Detect Prey 17 (6):619-27; Kennedy, 1994, J Natl Cancer Inst 86 (16):1185-6; Kirn, 1996, Mol Med Today 2 (12):519-27; Lorence, 1994, J Natl Cancer Inst 86 (16):1228-33; Lorence, 1994, Cancer Res 54 (23):6017-21; Batliwalla, 1998, Mol Med 4 (12):783-94; Reichard, 1992, J Surg Res 52 (5):448-53; Schirrmacher, 1998, Semin Oncol 25 (6):677-96; Moss, 1996, J Naturopathic Med 6 (1):23-32). The NDV belongs into the family of lipid bi-layer containing viruses having a diameter of 150 to 300 nm. Its genome consists of 15 kb RNA of negative polarity. The genome comprises the following 6 genes (in 3" to 5' direction): nucleocapsid protein (NP, 55 kDa), phosphoprotein (P, 53 kDa), matrix protein (M, 40 kDa), fusion protein (F, 67 kDa), hemagglutinin-neuromimidase (HN, 74 kDa) and Large protein (L, 200 kDa) (Nagai 1998). The surface proteins HN and F are glycosylated transmembrane proteins. The matrix protein serves as an anchor for the genome and the genome-associated proteins NP, P and L, the latter ones forming the nucleocapsid of the NDV. The fusion protein (F) is also a glycoprotein which is synthesized as an inactive precursor ($F_0$, 67 kDa) which is proteolytically cleaved into a biologically active protein consisting of two disulphide bond-linked chains ($F_1$, 55 kDa and $F_2$, 12.5 kDa) (Phillips, 1998). The cleavage sequence of the F protein and the length of the HN protein are the pivotal parameters responsible for the virulence of an NDV strain (Romer-Oberdorfer, 2003). Specifically, non-virulent NDV strains do not have cleavage sites in their $F_0$ proteins. It has been recently found that NDV is capable of replicating in human neoplastic cells better than in non-neoplastic human cells (Pecora, 2002, Schirrmacher, 1999, Reichert, 1992). Accordingly, the virus is an interesting candidate for a virus-based anti-cancer therapy. Moreover, it has been found that the selective replication of the NDV is independent of the proliferation of the target cell population. Accordingly, even slowly growing cells can be efficiently infected (Schirrmacher, 1998). Since NDV is not harmful for humans and mechanisms of adaptation of NDV to the human immune system have not yet been described, there are no substantial concerns regarding the use of NDV for therapeutic purposes in humans (Schirrmacher, 2005).

More recently, a therapeutic approach has been described which combines virus-based therapy and targeting. In said approach, viruses are delivered to the tumor cells by tumor-specific T cells as a carrier. Specifically, tumor-specific T cells were obtained from a patient and were loaded ex vivo with intact virus. Subsequently, the loaded tumor-specific T cells were autologously administered to the patient where they delivered the virus to the site of the tumor. This approach is also known as "viral hitch-hiking". (Cole, 2005, Nature Med 11 (10):1973-1081; Rooney, 2005, Nature Med 11 (10):1051-1052; Thorne, 2006, Science 311:1780-1784) This approach, thus, allows a targeted application of NDV rather than a mere systemic administration. However, the immune response induced against the tumor is still rather weak and inefficient as reported for the systemic administration. (Schirrmacher, 2001, Int J Oncol 18:945-952)

Accordingly, means and methods for an efficient and reliable immunotherapy of tumors and, in particular, solid tumors have no yet been described but are nevertheless highly desirable.

The technical problem underlying the present invention can be seen as the provision of means and methods for an efficient and reliable targeting based immunotherapy of cancer complying with the aforementioned needs. The technical problem is solved by the embodiments characterized in the claims and herein below.

BRIEF SUMMARY OF THE INVENTION

Accordingly, the present invention provides a method of treating a tumor in a subject comprising administering to the subject suffering from the said tumor in a therapeutically effective amount an antibody fusion protein which specifically recognizes (i) the VA, HN or F surface antigen of the Newcastle disease virus (NDV) and
(ii) a surface molecule of a tumor-unspecific T cell or a surface molecule of a dendritic cell.

DETAILED DESCRIPTION OF THE INVENTION

Figure 1:
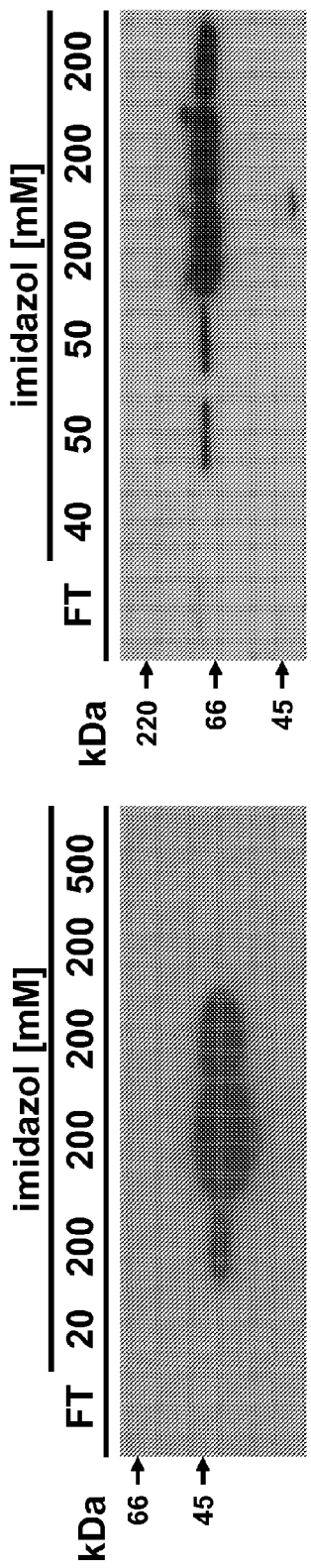
FIG. 1 shows Western blots of the eluates of these column purifications for different recombinant antibody fusion proteins according to the present invention. The eluted fractions were separated by SDS-PAGE, electroblotted onto nitrocellulose membranes, and probed first with an anti-Flag or anti-E-tag monoclonal antibody (mAb) and then with a horseradish peroxidase (HRP)-conjugated goat anti-mouse IgG antibody. The detection was carried out with the help of the ECL technique. The bispecific (bs) proteins bsHN-IL-2 and bsF-CD28 have the expected molecular weight of 45 and 66 kDa, respectively, while the trispecific (ts) proteins tsHN-IL-2-CD28 and tsF-IL-2-CD28 have the expected molecular weight of 80 kDa.
Figure 1:
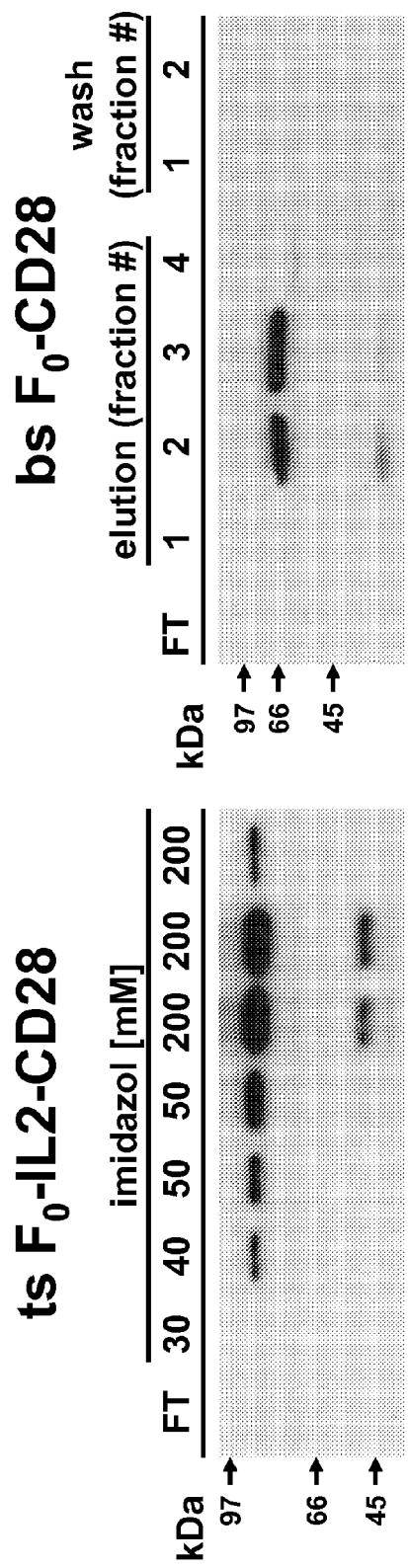

The term "subject" as used herein refers to animal, preferably, to mammals including pets such as dogs, cats, horses, laboratory animals such as mice and rats, and farming animals such as cows, pigs, sheep or goat. More preferably, the term relates to humans.

The term "treating" as used herein encompasses an entire successful treatment of the tumor (i.e. destruction of the tumor) as well as amelioration of the tumor (i.e. reduction of the tumor size or number of the tumor cells to a statistically significant degree). Moreover, it is to be understood that a successful treating—although preferably envisaged—will not occur in all patients subject to the aforementioned therapy. However, it is envisaged that a statistically significant portion of a population of subjects suffering from the tumor can be successfully treated. Whether a portion is statistically significant can be determined by various statistical tests known in the art such as the Student's t-test. Preferred p-values as indicators of a significant treatment result are p=0.1, 0.05, 0.01, 0.001 or 0.0001. Further details on such statistical evaluations are to be found in Dowdy and Wearden, Statistics for Research, John Wiley & Sons, New York 1983. The success of treatment can be monitored by conventional techniques of tumor diagnosis including determination of the number of tumor cells or the tumor size.

The term "therapeutically effective amount" refers to an amount of the antibody fusion protein which ameliorates or destroys the tumor. Preferred therapeutically effective amounts and suitable modes of administration for the antibody fusion protein are specified elsewhere in this description.

The term "tumor" as referred to in accordance with the present invention is, preferably, a solid tumor. More preferably, it is a carcinoma of breast, colon, rectum, lung, head, neck, kidney, or ovary, or a glioblastoma. The term also encompasses metastases of the said tumors.

The term "antibody fusion protein" as used herein refers to a protein comprising antigen recognizing domains of antibodies which are capable of specifically recognizing the different antigens specified above, i.e. the antibody fusion protein comprises the antigen recognizing domains of (i) an antibody which specifically recognizes the VA, HN or F antigen of NDV and (ii) an antibody which specifically recognizes a surface molecule of a tumor-unspecific T cell, or a surface molecule of a dendritic cell. Such molecules are also referred to as bispecific antibodies The antigen recognizing domains referred to herein, preferably, comprise at least the complementary determining regions (CDRs) of an antibody specifically recognizing an antigen as referred to above. More preferably, the antigen recognizing domain comprises the variable regions of the heavy chain ($V_H$) and the variable regions of the light chain ($V_L$). The antibody fusion protein, preferably, further comprises a cytokine; see also below.

The term "specifically recognizing" as used in accordance with the present invention refers to the capability of an antigen recognizing domain to specifically bind the antigen in significant amounts. Thus, if the antibody fusion protein of the present invention comprising the aforementioned antigen recognizing domains is brought into contact with a mixture of various different proteins including the antigens, it is envisaged that the antibody fusion protein will exclusively or at least pivotally bind to the antigens. Binding of the antibody fusion protein, if any, to other proteins contained by the mixture (i.e. cross-reactivity) will occur only in statistically insignificant amounts, preferably, amounts below the boarder of detection. Techniques for determining cross-reactivity are well known in the art.

The first antigen recognizing domain of the antibody fusion protein specifically recognizes the VA, HN or F surface antigen of NDV. It is to be understood that the aforementioned surface antigens must not be derived from a specific strain, rather, in accordance with the present invention all NDV strains including oncolytic strains may be used as a source of the said VA, HN or F surface antigen. Particularly suitable strains have been described in www.cancer.gov/cancertopics/pdq/cam/NDV/HealthProfessional. The surface antigens of NDV can be obtained by protein purification techniques or by recombinant manufacture. Preferably, it is envisaged that the antigen recognizing domain recognizes an epitope of the VA, HN or F surface antigen which is available for binding by the antibody fusion protein on intact NDV. Accordingly, the epitope shall not be selected from the transmembrane or membrane anchoring part of the aforementioned surface antigens. More preferably, an epitope to be specifically recognized by the antibody fusion protein according to the present invention is derived from the following parts of the surface molecules (Gotoh, 1988, Virology 163 (1):174-182 (accession number: GI:332375); Pritzer, 1990, Virus Res 15 (3): 237-242 (accession number: GI:60658)).

It is to be understood that the aforementioned epitopes are also, preferably, to be used for generating the antibody from which the antigen recognizing domain is to be obtained.

The second antigen recognizing domain of the antibody fusion protein according to the present invention specifically recognizes a surface molecule of a tumor-unspecific T cell. "Tumor-unspecific T cells", as referred to in accordance with the present invention, are T cells, which do not specifically recognize tumor antigens. Preferably, such T cells are cytotoxic T cells or memory T cells. These tumor-unspecific T cells can be obtained by methods well known in the art. (Haas 2005, Vaccine 23:2439-2453; Haas 2005, Int J Cancer, March 1, 118 (3):658-67). Preferably, the surface molecule of the tumor-unspecific T cell referred to in accordance with the present invention is selected from the group consisting of CD2, CD5, CD9, CD11A, CD25 (IL-2 receptor alpha-chain), CD26, CD28, CD29, CD43, CD44, CD45 RO, CD45 RA, CD45 RB, CD47, CD58 (LFA-3), CD69, CXCR4, CD107a, CD122 (IL-2 receptor beta-chain), CD132 (IL-2 receptor gamma-chain) and CD247. The amino acid sequences of the said surface molecules are well known in the art. Preferred amino acid sequences are described in the following table:

| Gene symbol | Gene bank (Acc. No.) | Gene bank (GI) | mRNA (length AS) | Complete cds | Remarks |
|---|---|---|---|---|---|
| CD2 | M16336 | 180093 | yes (360) | yes | |
| CD5 | BC027901 | 20379742 | yes (495) | yes | |
| CD9 | M38690 | 1048988 | yes (228) | yes | |
| CD11a | BC008777 | 33870544 | yes (1086) | yes | |
| CD25 | M14098 | 186307 | yes (251 [with signal peptide 272]) | no | mature peptide, without signal peptide |
| CD26 | MM74777 | 180082 | yes (766) | yes | |
| CD28 | J02988 | 338444 | yes (220) | yes | |
| CD29 | DQ891069 | 113708294 | yes (825) | yes | |
| CD43 | BC012350 | 15214445 | yes (400) | yes | |
| CD44 | BC004372 | 13325117 | yes (699) | yes | |
| CD45 | BC014239 | 33878494 | yes (756 [acc. to ref. seq. 1304]) | no | see encl. (ref. seq.: NM_002838/NP_002829) |
| CD47 | BC037306 | 22713603 | yes (305) | yes | C-ter (20AS) different to ref. seq. (NP_001768: 323AS) |
| CD58 | BT019817 | 54696495 | yes (250) | yes | |
| CD69 | BC007037 | 13937862 | yes (199) | yes | |
| CXCR4 | BC020968 | 34189293 | yes (352) | yes | |
| CD107a | J04182 | 186927 | yes (416) | yes | LAMP-1 |
| CD122 | M26062 | 186322 | yes (551) | yes | IL-2R $\beta$ |
| CD132 | BC014972 | 15929027 | yes (369) | yes | common $\gamma_c$ |
| CD247 | BC025703 | 19344013 | yes (164) | yes | TCR $\zeta$-chain |

The surface antigens can be obtained by protein purification techniques or by recombinant manufacture. Preferably, it is envisaged that the antigen recognizing domain recognizes an epitope of the surface antigens which is available for binding by the antibody fusion protein on intact tumor-unspecific T cells. Accordingly, the epitope shall be, preferably, selected from the extracellular and exposed portion of the aforementioned surface antigens. It is to be understood that the aforementioned epitopes are also, preferably, to be used for generating the antibody from which the antigen recognizing domain is to be obtained.

Alternatively, the second antigen recognizing domain of the antibody fusion protein shall specifically recognize a surface molecule of a dendritic cell of the immune system. The "dendritic cells" of the immune system are stimulators of the T cell mediated immune response (Bonasio, 2006, Curr Opin Immunol, August, 18 (4):503-11). How to obtain dendritic cells is well known in the art. Preferably, said surface molecule of dendritic cells referred to in accordance with the present invention is CD1a/b, CD11c, CD16a, CD40, CD68, CD80, CD83, CD86, IFNAR1 (interferon-alpha/beta receptor), CD119 (interferon-gamma receptor 1), CDB197 (CCR7), CD205 (DEL-205), CD209 (DC-SIGN) and CD227 (MUC1). The amino acid sequences of the said surface molecules are well known in the art. Preferred amino acid sequences are described in the following table:

| Gene symbol | Gene bank (Acc. No.) | Gene bank (GI) | mRNA (length AS) | Complete cds | Remarks |
|---|---|---|---|---|---|
| CD1a | M28825 | 180035 | yes (327) | yes | |
| CDb | M28826 | 180055 | yes (333) | yes | |
| CD11c | M81695 | 487829 | yes (1163) | yes | |
| CD16a | BC036723 | 22477183 | yes (290) | yes | |
| CD40 | BC012419 | 15214586 | yes (277) | yes | |
| CD68 | BC015557 | 33869409 | yes (354) | yes | |
| CD80 | BC042665 | 27503575 | yes (288) | yes | |
| CD83 | BC030830 | 21410826 | yes (205) | yes | |
| CD86 | BC040261 | 25955518 | yes (329) | yes | |
| IFNAR1 | BC021825 | 18255501 | yes (557) | yes | binds IFN-α/β/ω |
| CD119 | BC005333 | 13529118 | yes (489) | yes | IFNGR1 |
| CD197 | BC035343 | 23243433 | yes (378) | yes | CCR7 |
| CD205 | AF064827 | 3695054 | yes (1722) | yes | DEC-205 |
| CD209 | M98457 | 187115 | yes (404) | yes | DC-SIGN |
| CD227 | J05581 | 188869 | yes (475) | yes | MUC1 discrepancy in the seq. length (1255 AA in ref. seq. > repetitive structures |

The surface antigens can be obtained by protein purification techniques or by recombinant manufacture. Preferably, it is envisaged that the antigen recognizing domain recognizes an epitope of the surface antigens which is available for binding by the antibody fusion protein on intact dendritic cells. Accordingly, the epitope shall be, preferably, selected from the extracellular and exposed portion of the aforementioned surface antigens. It is to be understood that the aforementioned epitopes are also, preferably, to be used for generating the antibody from which the antigen recognizing domain is to be obtained.

How to combine said different antigen recognizing domains of antibodies and, in a preferred embodiment of the method of the present invention, the said cytokine to an antibody fusion protein is, in principle, well known in the art and has been described for bispecific antibodies in, e.g. (Dela Cruz, 2004, Clin Exp Med, October, 4(2):57-64). Moreover, further details on how to combine the antigen recognizing domains to an antibody fusion protein of the present invention can be found in the accompanying Examples, below. In principle, the antibody fusion protein of the present invention can be made as follows: antibodies which specifically recognize the aforementioned antigens or epitope-containing fragments thereof and which can be used as a source for antigen recognizing domains to be combined to the antibody fusion protein of the present invention can be made by conventional techniques for making antibodies. Preferably, the antibodies are generated as monoclonal antibodies. Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals. Furthermore, antibodies as referred to herein can be obtained by using methods which are described, e.g., in Harlow and Lane "Antibodies, A Laboratory Manual", CSH Press, Cold Spring Harbor, 1988. Specific antigens which are, preferably, to be used for generating the antibodies are specified below. The nucleic acid sequences encoding the antigen recognizing domains of said antibodies can be obtained by standard molecular biology techniques, including, e.g., PCR, molecular cloning and sequencing. Similarly, nucleic acid sequences of a cytokine can be obtained. The nucleic acid sequences thus obtained shall be combined to a single polynucleotide by standard molecular biology techniques. Subsequently, a recombinant polynucleotide comprising the nucleic acid sequences of the two antigen recognizing domains shall be used for the recombinant production of the antibody fusion protein of the present invention. Alternatively, antibodies or antibody fragments comprising the individual antigen recognizing domains can be chemically linked by cross-linking agents known in the art. Such chemically linked entities are also antibody fusion proteins according to the present invention.

Single chain (scFv) antibodies are, preferably, used to obtain the antibody fusion protein. Moreover, to avoid harmful or undesired reactions of the immune system against the antibody fusion protein, it is envisaged that the antibody fusion protein is, preferably, a humanized antibody fusion protein comprising a humanized antibody amino acid sequence. Humanized antibody amino acid sequences can be obtained by methods well known in the art.

Moreover, it is to understand that in the method of the present invention a polynucleotide encoding the aforementioned antibody fusion protein may be administered instead or in addition to the antibody fusion protein. Furthermore, the antibody fusion protein may be bound to the said tumor-unspecific T cells or dendritic cells when being administered. In other words, tumor-unspecific T cells or dendritic cells being bound to the antibody fusion protein may be administered instead or in addition to the antibody fusion protein.

In a preferred embodiment of the method of the present invention, said tumor has been infected by the NDV prior to administration of the antibody fusion protein, the polynucleotide, the tumor-unspecific T cell or the dendritic cell. Infection of a tumor by NDV is, preferably, achieved by administration of virus loaded tumor antigen-specific T cells as a carrier for the NDV. Accordingly, prior to the administration of the antibody fusion protein, polynucleotide and/or cells referred to in accordance with the method of the present invention, tumor antigen specific T cells are, preferably, obtained from the subject to be treated and loaded by intact NDV. To this end, the tumor-specific T cells are bound to NDV via a surface molecule. Subsequently, these loaded tumor antigen specific T cells are administered back into the patient. Due to the tumor antigen specificity of the T cells, the NDV will be delivered to the tumor cells. The tumor cells than become infected by the NDV and will start to express the NDV surface antigens VA, HN and/or F referred to above in detail. Now, the antibody fusion protein or the above mentioned cells will upon administration be targeted to the NDV surface molecule expressing tumor cells and elicit an immune response as set forth above.

NDV strains to be used for infection may be lentogenic, mesogenic or velogenic strains. Preferred are those strains which have a strong oncolytic capacity because these strains further assist in the destruction of the tumor. Moreover, a recombinant NDV may be used which upon infection of the tumor cells expresses genes being harmful or toxic for the infected tumor cell. Preferred genes to be expressed are genes encoding cytokines, tumor suppressor genes or apoptosis-inducing genes. Preferred cytokines are interleukin 2 (IL-2), interleukin 4 (IL-4), interleukin 6 (IL-6), interleukin 12 (IL-12), interleukin 15 (IL-15), granulocyte colony stimulating factor (G-CSF), granulocyte and macrophage colony stimulating factor (GM-CSF), interferon alpha, beta or gamma and tumor necrosis factor (TNF). Preferred tumor suppressor genes are p53, Rb, p16$^{INK4a}$, APC (adenomatous polyposis coli), DCC (Deleted in Colon Carcinoma), TSLC1. Preferred apoptosis inducing genes are bcl-2, bax, ICE proteases. How to make such a recombinant NDV strain is well known in the art, see, e.g., Conzelmann, 1998, Annu Rev Genet. 32:123-62; Roberts, 1998, Virology 20, 247 (1):1-6. Therefore, the present invention also encompasses a recombinant NDV comprising in its viral genome a polynucleotide encoding at least one the aforementioned genes.

Advantageously, the method of the present invention allows specifically targeting the tumor destroying cells of the immune system, i.e. the tumor-unspecific T cells (e.g., cytotoxic T cells) or dendritic cells, to virus infected tumor cells in a subject upon administration. Thus, it combines the effects of a virus-based cancer therapy with an efficient immune response against the tumor.

The present invention also relates to an antibody fusion protein which specifically recognizes
(i) the VA, HN or F surface antigen of the Newcastle disease virus (NDV), and
(ii) a surface molecule of a tumor-unspecific T cell or a surface molecule of a dendritic cell,
wherein said antibody fusion protein further comprises a cytokine.

An antibody fusion protein which is capable of specifically recognizing the aforementioned antigens has been described already above in detail.

A "cytokine" as referred to in accordance with the present invention is a member of the cytokine protein family. The cytokine shall be capable of eliciting or enhancing an immunological response against tumor cells. Preferably, the cytokine referred to herein is selected from the group consisting of interleukin 2 (IL-2), interleukin 4 (IL-4), interleukin 6 (IL-6), interleukin 12 (IL-12), interleukin 15 (IL-15), granulocyte colony stimulating factor (G-CSF), granulocyte and macrophage colony stimulating factor (GM-CSF) interferon alpha, beta or gamma and tumor necrosis factor (TNF). Most preferably, the cytokine referred to herein is IL-2.

In principle, there is no distinct order of the three components of the antibody fusion protein required. However, functional activity requires correct folding of the protein. Correct folding can be tested by functional tests to select the most effective constructs. Preferably, the cytokine shall be flanked by the two antigen recognizing domains referred to in accordance with the present invention. Variants of antibody fusion proteins of the present invention may be tested for the biological activities by using the assays described in the accompanying Examples.

Advantageously, the aforementioned antibody fusion protein of the present invention may be used in virus cancer therapies using the promising NDV. Upon administration, the antibody fusion proteins attract tumor-unspecific T cells to the tumor cells in a subject to be treated, preferably, in a human. Due to the attraction of tumor-unspecific T cells, such as cytotoxic or memory T cells, and the immune response stimulating effects of the cytokine portion of the antibody fusion protein, an efficient immune response is elicited at the site of the tumor in the subject. In the present study, it has been demonstrated that antibody fusion proteins comprising a cytokine which are targeted to a virus-modified tumor vaccine are capable of augmenting its T cell stimulatory capacity. A tumor vaccine, optimally modified by virus-specific recombinant proteins is shown to fully activate naïve T cells so that these can exert durable anti-tumor activity against non-virus infected bystander tumor cells. Parameters of importance for anti-tumor activity or tumor vaccine efficiency are: 1) time of vaccine application (adjuvant situation rather than late stage disease), 2) activation of a polyclonal memory T cell response including CTL and delayed type hypersensitivity T cells and 3) mobilization of tumor infiltrating T lymphocytes. The antibody fusion protein of the present invention will be able to activate not only anti-tumor memory T cells but also anti-tumor activity from naïve T cells.

The present invention also pertains to a polynucleotide encoding the antibody fusion protein of the present invention. As discussed above, the said polynucleotide may be used for the recombinant production of the antibody fusion protein of the present invention or may be used for gene therapy based approaches. The polynucleotide may be expressed in a subject to be treated by the targeting based therapeutic approach specified elsewhere in this description. It is to be understood that the polynucleotide may be comprised by a vector or a targeting construct. Usually, the polynucleotide shall be operatively linked to an expression control sequence in such a vector or targeting construct. The expression control sequence shall allow expression in a host cell which is used for recombinant production or may allow expression in a subject to be treated.

It follows from the above that the present invention also encompasses a tumor-unspecific T cell being bound by the antibody fusion protein of the present invention. Preferably, the antibody fusion protein is bound to a surface molecule of the said tumor-unspecific T cell. More preferably, said surface molecule is selected from the group consisting of: CD2, CD5, CD9, CD11a, CD25 (IL-2 receptor alpha chain), CD26, CD28, CD29, CD43, CD44, CD45 RO, CD45 RA, CD45 RB, CD47, CD58 (LFA-3), CD69, CXCR4, CD107a, CD122 (IL-2 receptor beta-chain), CD132 (IL-2 receptor gamma-chain), and CD247.

Furthermore, the present invention includes a dendritic cell being bound by the antibody fusion protein of the present invention. Preferably, the antibody fusion protein is bound to a surface molecule of the dendritic cell and, more preferably, to a surface molecule being selected from the group consisting of: CD1a/b, CD11c, CD16a, CD40, CD68, CD80, CD83, CD86, CD118 (Interferon alpha/beta receptor), CD119 (Interferon gamma to receptor), CDw197, CD205, CD209, and CD227.

In accordance with the present invention it has been found that the aforementioned antibody fusion protein, polynucleotide and/or cells (i.e. tumor-unspecific T cells or dendritic cells bound to the antibody fusion protein) of the present invention upon administration to a cancer patient significantly improve a virus-based cancer therapy, in particular, in the case of solid tumors. Therefore, the present invention relates, furthermore, to a pharmaceutical composition comprising the antibody fusion protein, the polynucleotide, the tumor-unspecific T cell or the dendritic cell of the present invention.

The term "pharmaceutical composition" as used herein comprises the substances or cells of the present invention and, optionally, one or more pharmaceutically acceptable carrier. The substances of the present invention may be formulated as pharmaceutically acceptable salts. Acceptable salts comprise acetate, methylester, HCl, sulfate, chloride and the like. The pharmaceutical compositions can be conveniently administered by any of the routes conventionally used for drug administration, for instance, orally, topically, parenterally, or by inhalation. The substances may be administered in conventional dosage forms prepared by combining the drugs with standard pharmaceutical carriers according to conventional procedures. These procedures may involve mixing, granulating, and compressing or dissolving the ingredients as appropriate to the desired preparation. It will be appreciated that the form and character of the pharmaceutically acceptable character or diluent is dictated by the amount of active ingredient with which it is to be combined, the route of administration, and other well-known variables. The carrier(s) must be "acceptable" in the sense of being compatible with the other ingredients of the formulation and not deleterious to the recipient thereof. The pharmaceutical carrier employed may be, for example, either a solid or liquid. Exemplary of solid carriers are lactose, terra alba, sucrose, talc, gelatine, agar, pectin, acacia, magnesium stearate, stearic acid, and the like. Exemplary of liquid carriers are phosphate buffered saline (PBS) solution, syrup, oil such as peanut oil and olive oil, water, emulsions, various types of wetting agents, sterile solutions, and the like. Similarly, the carrier or diluent may include time delay material well known to the art, such as glyceryl mono-stearate, or glyceryl distearate alone or with a wax. The substance according to the present invention can be administered in various manners to achieve the desired effect. Said substance can be administered either alone or in the formulated as pharmaceutical preparations to the subject being treated either orally, topically, parenterally, or by inhalation. Moreover, the substance can be administered in combination with other substances either in a common pharmaceutical composition or as separated pharmaceutical compositions. The diluent is selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers, and the like. For making those formulations the active substance(s) will usually be mixed with a carrier or diluted by a diluent, or enclosed or encapsulated in a capsule, sachet, cachet, paper, or other suitable containers or vehicles. A carrier may be solid, semisolid, gel-based, or liquid material which serves as a vehicle, excipient or medium for the active ingredients. Said suitable carriers comprise those mentioned above and others well known in the art, see, e.g., Remington's Pharmaceutical Sciences, Mack Publishing Company, Easton, Pa. The formulations can be adapted to the mode of administration comprising the forms of tablets, capsules, suppositories, solutions, suspensions, or the like. A therapeutically effective dose refers to that amount of the substance according to the invention which ameliorates the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. The dosage regimen will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. A typical dose can be, for example, in the range of 1 to 1000 µg per day. However, doses below or above this exemplary range are envisioned, especially considering the aforementioned factors. Generally, the regimen as a regular administration of the pharmaceutical composition should be in the range of 1 µg to 10 mg units per day. If the regimen is a continuous infusion, it should also be in the range of 1 µg to 10 mg units per kilogram of body weight per minute, respectively. Progress can be monitored by periodic assessment. However, depending on the subject and the mode of administration, the quantity of substance administration may vary over a wide range to provide from about 0.01 mg per kg body mass to about 10 mg per kg body mass. The cells of the present invention can be administered as pharmaceutical compositions in pharmaceutically acceptable cell culture media or isotonic saline solutions. The pharmaceutical compositions referred to herein are administered at least once in accordance with the use of the present invention. However, the said pharmaceutical compositions may be administered more than one time, for example from one to four times daily up to a non-limited number of days.

Thus, the present invention encompasses the use of the antibody fusion protein, the polynucleotide, the tumor-unspecific T cell or the dendritic cell of the present invention for the manufacture of a pharmaceutical composition as referred to above for treating a tumor having tumor cells expressing the VA, HN or F surface antigen of NDV. Preferably, said tumor has been infected by the NDV. More preferably, in order to infect the said tumor by the NDV, tumor-specific T cells having bound the NDV are to be administered. As already referred to above, the tumor according to the use of the present invention is, preferably, a solid tumor. More preferably, it is a carcinoma of breast, colon, rectum, lung, head, neck, kidney, or ovary or a glioblastoma. The pharmaceutical composition of the present invention can be specifically manufactured for use in the method of the present invention. To this end, the antibody fusion protein, the polynucleotide or the cells of the present invention specified above may be packaged together in separate vials as a kit of parts. The individual components of said kit are adopted for combined application in the method according to the present invention. The kit may, preferably, include instructions for carrying out the method according to the present invention.

All references referred to above are herewith incorporated by reference with respect to their entire disclosure content as well as their specific disclosure content explicitly referred to in the above specification.

The figures show:

The invention will now be illustrated by the following Examples which shall, whatsoever, not be construed to limit the scope.

EXAMPLE 1

Production and Characterization of Recombinant Antibody Fusion Proteins

For the production of recombinant fusion proteins in dihydrofolate reductase (dhfr) deficient Chinese hamster ovary (dCHO) cells, a vector which was kindly provided by P. Bäuerle (Micromet GmbH, Martinsried, Germany) was modified. The plasmids encoding the bispecific constructs bsHN-CD3 (#242) and bsHN-CD28 (#290) (Haas 2005, Vaccine 23: 2439-2453), as well as bsHN-IL-2 (#356) (Bian, 2005, Cancer Gene Ther 12, 295-303) have been described. The trispecific construct tsHN-IL-2-CD28 (#716) contains the human IL-2, derived from the plasmid pFc54.t (ATCC, Rockville, USA) which was cloned between the anti-HN and anti-CD28 single chain variable fragment (scFv) portions of plasmid #290.

The F-specific scFv (#614) was elaborated from a phage library into which the scFv from spleen cells of a mouse that had been immunized against NDV was cloned. The trispecific construct tsF-IL-2-CD28 (#770) was obtained from plasmid #716 by replacing the anti-HN scFv against the anti-FscFv plasmid #614. The construct bsF-CD28 (#337) was likewise obtained by replacing the anti-HN scFv (of plasmid #290) against the anti-F scFv from plasmid #614. All constructs were cloned upstream the dhfr gene and downstream of the cytomegalovirus (CMV) promoter in such a way that the expression of both genes in the cistron remained under the control of the same elongation factor promoter (hEF-A). The restriction enzymes and the corresponding buffers were bought from New England Biolabs (Frankfurt a. M., Germany). The T4 DNA ligase was obtained from Roche (Mannheim, Germany).

The amplification of the DNA plasmids was performed in TOP-10 bacteria, grown in LB medium (Applichem, Darmstadt, Germany) containing 100 µg/ml ampicillin (Sigma-Aldrich, Schnelldorf, Germany). Transfection of the plasmids into cells was carried out by electroporation (Biorad, Munich, Germany) according to standard protocol. Clones that were stably expressing the desired fusion protein in an efficient way were selected by liming dilution technique. The production was conducted in high density cell culture systems (Integra Biosciences, Fernwald, Germany) according to the manufacturer's recommendations.

The fusion proteins containing a $His_6$-tag at their C-terminus were purified by immobilized metal affinity chromatography (IMAC), in particular by nitrilotriacetic acid (NTA)-chelated $Ni^{2+}$ ions coupled to an agarose matrix (Qiagen, Hilden, Germany), as described (Haas et al., 2005). Briefly, the Integra medium containing the soluble protein of interest was dialyzed overnight at 4° C. in binding buffer (50 mM $NaH_2PO_4*H_2O$, 300 mM NaCl; pH 8.0), before being supplemented with 20 mM imidazole (all chemicals from Merck, Darmstadt, Germany) and being incubated with the nickel beads (for 2 hr at 4° C. on a rotator). The beads were loaded onto a column and washed extensively with wash buffer (50 mM $NaH_2PO_4*H_2O$, 300 mM NaCl, 20 mM imidazole; pH 8.0). The bound proteins were eluted from the column by increasing the imidazole concentration within the wash buffer stepwise from 20 to 30, 40, 50 and finally to 200 mM. The eluted proteins were collected in 2 ml fractions. The purification of the E-tag containing protein (bsF-CD28) was performed by means of an anti-E-tag immunoaffinity chromatography procedure (Amersham Biosciences, Freiburg, Germany). The protein, binding to the column at neutral pH and high salt concentration, was eluted in 2 ml fractions by simultaneously lowering the pH and the salt concentration (according to manufacturer's instructions).

The purity of the different fractions was assessed by Coomassie staining (with the GelCode® Blue Stain Reagent from Pierce, Bonn, Germany) after separation of the purified proteins on 12.5% SDS-PAGE gels. The size of the molecules was checked by Western blot. The fractions exhibiting the highest purity and protein amount were pooled, dialyzed against PBS overnight at 4° C. (to remove imidazole), filtered (0.22 µm) and stored at −80° C. The concentrations of the purified proteins were determined using the CB-Protein Assay™ reagent (Calbiochem, Schwalbach, Germany) and using bovine serum albumin (BSA) as reference protein.

The IL-2 activity of the fusion proteins was quantified by means of the IL-2 growth factor-dependent human T cell lymphoma line CTLL. Briefly, CTLL cells were set cytokine-free for 24 hr, before being distributed into 96-well microtiter plates ($1 \times 10^4$ cells/well in 100 µl). The fusion proteins, serially pre-diluted in PBS, were added in 100 µl/well. After a 20 hr incubation at 37° C. in a 5% $CO_2$ incubator, 1 µCi [$^3$H]-thymidine (Amersham Biosciences, Freiburg, German) was added per well for a further 4 hr incubation. Incorporation of radioactivity into the DNA was determined by adsorbing the cells onto glass fiber filters (PerkinElmer Wallac, Freiburg, Germany) with the use of a micro cell harvester (Tomtec; PerkinElmer Wallac, Freiburg, Germany). After drying, the filters were counted in scintillation fluid by means of an automatic liquid scintillation β-counter (PerkinElmer Wallac, Freiburg, Germany). Mean counts per minute (cpm) were calculated from duplicates. Recombinant human IL-2 (Chiron Therapeutic, Emeryville, USA) served as reference.

The murine hybridoma cell lines producing the IgG2a anti-NDV-HN(HN.B) and the IgG1 anti-NDV-F (Icii) mAbs were kindly provided by Dr. R. M. Iorio (Department of Molecular Genetics and Microbiology, University of Massachusetts, Medical School, USA). The mouse hybridoma cell line producing mAb 9.3 (recognizing the human CD28 molecule) was obtained from Dr. J. A. Hansen (Fred Hutchinson Cancer Research Center, Seattle, USA; Damle et al., 1981 (PNAS: 5096-5098)). These hybridoma cells were maintained in RPMI-1640 medium supplemented with 10% fetal calf serum (FCS), 2 mM L-glutamine, 10 mM HEPES, 100 U/ml penicillin and 100 µg/ml streptomycin. All growth media and supplements were purchased from Gibco Invitrogen (Karlsruhe, Germany), unless otherwise mentioned. The anti-EpCAM antibody (HEA-125) was a kind gift of Dr. G. Moldenhauer (DKFZ, Heidelberg, Germany). The allophycocyanin (APC)-conjugated anti-CD8, the fluorescein isothiocyanate (FITC)-conjugated anti-CD25 as well as the phycoerythrin (PE)-labelled anti-CD45RO and anti-CD107a mAbs were purchased from Becton Dickinson (BD) Pharmingen (Heidelberg, Germany). mAbs against $His_6$-tag, E-tag and Flag-tag were obtained from Dianova (Hamburg, Germany), Amersham Biosciences (Freiburg, Germany) and Sigma-Aldrich (Schnelldorf, Germany), respectively. PE-labelled goat F(ab')$_2$ anti-mouse IgG antibody was bought from Southern Biotech (Birmingham, USA). Horse radish peroxidase (HRP)-conjugated goat anti-mouse IgG antibody was purchased from Jackson ImmunoResearch (Cambridgeshire, England). PE-conjugated monoclonal antibody against murine CD25 and the corresponding PE-conjugated rat IgG1 monoclonal antibody as negative control were obtained from BD Pharmingen (Heidelberg, Germany).

The NDV-specific binding sites were directed either against the HN or against the F protein. In addition to NDV-specific IL-2 immunocytokines we constructed fusion proteins containing also an anti-CD28 binding site in order to provide a classical costimulatory signal (signal 2a). Recombinant fusion proteins were produced in dCHO cells, as described (Haas, 2005). Three proteins containing a His-tag were purified by IMAC (Ni-NTA-Sepharose) and one protein was purified by immuno-affinity chromatography using an anti-Etag column. FIG. 1 shows Western blots of the eluates of these column purifications. The recombinant proteins were identified with anti-Flag mAb and the ECL technique. The bispecific (bs) proteins bsHN-IL2 and bsF-CD28 have the expected molecular weight of 45 and 66 kDa, respectively, while the trispecific (ts) proteins tsHN-IL-2-CD28 and tsF-IL-2-CD28 have the expected molecular weight of 80 kDa.

Figure 2:
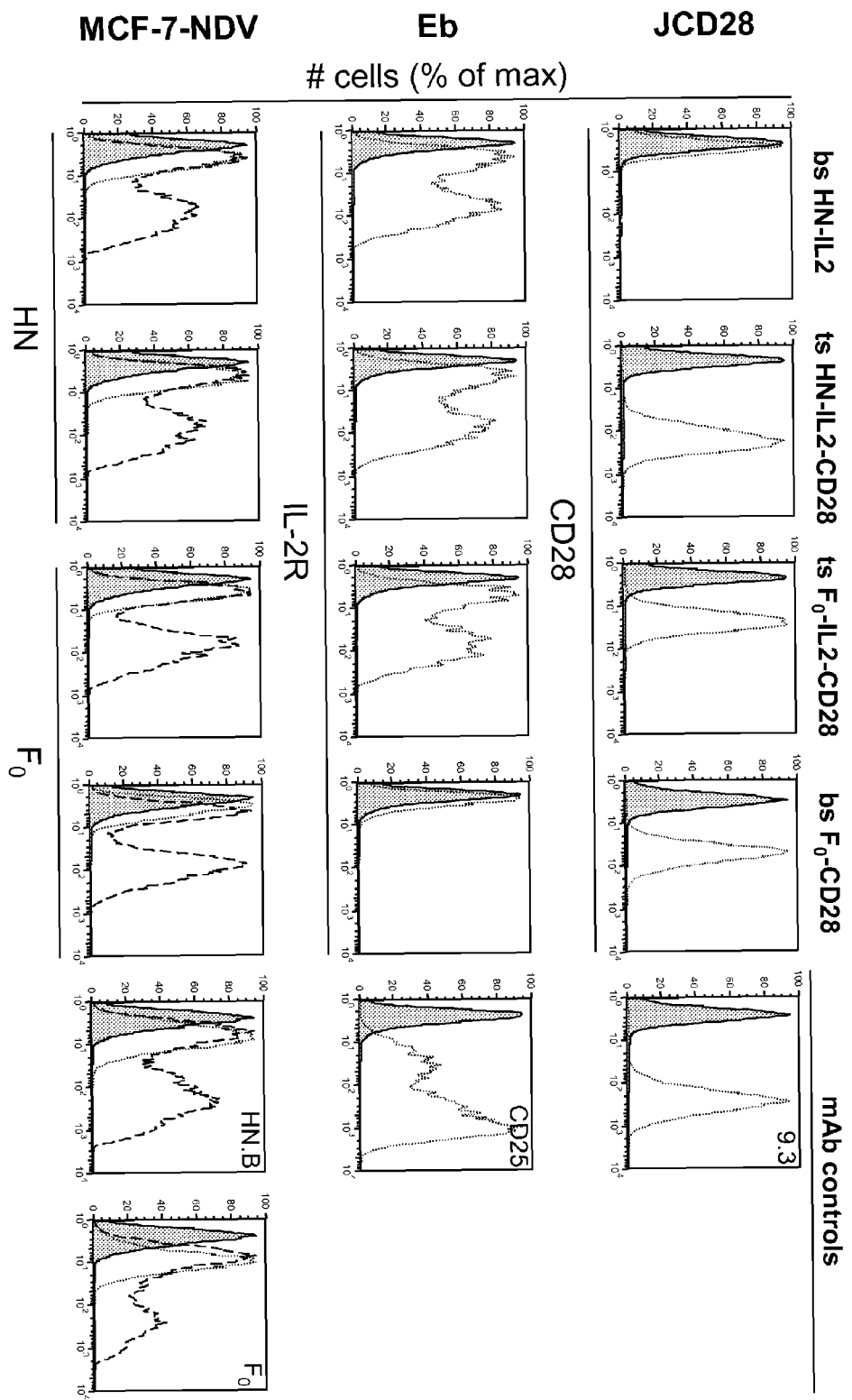
FIG. 2 shows FACS analyses with different recombinant antibody fusion proteins demonstrating the binding of the anti-HN or anti-FscFV portions to NDV-infected MCF-7 human breast carcinoma cells MCF-7-NDV (A) and the binding of the IL-2 cytokine and to anti CD28 scFv portion to pre-activated human T cells (B).

The binding specificity of the virus-specific antibody fusion proteins were analyzed by FACS analysis with cells expressing the respective target molecules. All constructs bound to NDV-infected MCF-7 human breast carcinoma cells (FIG. 2A) but not to uninfected cells (data not shown). The immunocytokines containing IL-2 bound specifically to IL-2 receptor positive murine Eb lymphoma cells. The CD28 binding site was demonstrated with CD28 expressing human Jurkat lymphoma cells (FIG. 2A). FIG. 2B shows the binding of IL-2 and anti CD28 to pre-activated human T cells. The protein tsHN-IL-2-CD28 has two binding sites which bound to IL-2 receptor at high density and to CD28 at medium density. FIG. 2B also shows the binding of the protein bsHN-CD3 and that is used to provide signal 1 through CD3/T cell receptor (TCR) activation. The bispecific antibodies bsHN-CD3 and bsHN-CD28 were shown before to activate T cells only when they can aggregate CD3 or CD28 molecules on the T cell surface. This does not occur with these monovalent reagents alone but only when they are attached through the anti-HN binding site to virus infected tumor cells. Table 1 gives an overview of the different antibody fusion proteins of this study: their code number, protein structure, protein concentration, their virus-binding activity expressed in arbitrary units and the biological IL-2 activity as determined by the growth of the IL-2 dependent CTLL T cell line. It can be seen that the F-specific proteins have a lower binding activity than the FIN-specific proteins but the IL-2 activity is similar.

TABLE 1

| protein No. | protein structure | protein amount | HN-/F₀- activity (U/ml) | IL-2 (U/ml) |
|---|---|---|---|---|
| 290 | bs HN-CD28 | 25.0 | $5.06 \times 10^5$ | 0.0 |
| 716 | bs HN-IL-2-CD28 | 49.6 | $2.03 \times 10^5$ | $1.6 \times 10^6$ |
| 356 | bs HN-IL2 | 103.3 | $2.03 \times 10^5$ | $1.4 \times 10^6$ |
| 337 | bs F-CD28 | 78.5 | $2.64 \times 10^4$ | 0.0 |
| 770 | ts F-IL-2-CD28 | 53.3 | $1.7 \times 10^4$ | $4.8 \times 10^6$ |

All cell lines were obtained from the tumor cell bank of the German Cancer Research Center (DKFZ; Heidelberg, Germany). Cell culture media were always supplemented with 2 mM L-glutamine, 10 mM HEPES, 100 U/ml penicillin and 100 μg/ml streptomycin (all purchased from GIBCO Invitrogen, Karlsruhe, Germany). The human breast carcinoma cell line MCF-7 was cultured in DMEM with 10% FCS. The human T cell lymphoma line Jurkat over-expressing CD28 (JCD28) and the murine T cell lymphoma line Eb were cultured in RPMI-1640 medium supplemented with 5 FCS. The human T cell lymphoma line CTLL was grown in ISCOVES medium containing 10% FCS and 25 U/ml recombinant human IL-2 (Chiron Therapeutic, Emeryville, USA). The murine fibroblast cell line Ltk.wt and the HN cDNA transfected Ltk.wt fibroblasts (Ltk.HN.A2) (Ertl 1993) were cultured in RPMI-1640 medium with 10% FCS. dCHO cells were grown in ISCOVES 'modified Dulbecco' medium (IMDM) supplemented with 10% FCS, $1 \times 10^4$ M hypoxanthine and $1.6 \times 10^{-5}$ M thymidine. After transfection, these cells were cultured in αMEM containing 5% dialyzed FCS (dFCS; Biochrom, Krefeld, Germany) and 10 nM methotrexate (Calbiochem, Schwalbach, Germany).

For the binding of the constructs to NDV surface antigens (HN or F), the human breast carcinoma cell line MCF-7 was infected for 24 hr with 100 hemagglutination units (HU) NDV per $1 \times 10^7$ cells. For the binding of the constructs to CD28 or the IL-2 receptor, the human T cell lymphoma line Jurkat, over-expressing the CD28 molecule (JCD28), and the murine T cell lymphoma line Eb were used, respectively. The cells, first incubated with the recombinant proteins, were stained with mouse anti-His₆-tag (Dianova, Hamburg, Germany) or mouse anti-E-tag (Amersham Biosciences, Freiburg, Germany) mAbs followed by PE-labelled goat F(ab')₂ anti-mouse IgG antibody (Southern Biotech, Birmingham, USA), as described (Haas et al., 2005). The cells were measured on a FACSCalibur fluorescence analyzer (Becton Dickinson, Heidelberg, Germany). For the analysis of human naïve T cell activation, up to $1 \times 10^6$ T lymphocytes were first blocked with endobulin (50 μg/μl; Baxter, Unterschleißheim, Germany), before being stained for 30 min on ice with APC-conjugated anti-CD8, FITC-conjugated anti-CD25, PE-conjugated anti-CD45RO or PE-conjugated anti-CD107a mAbs (all purchased from BD Pharmingen, Heidelberg, Germany). The cell measurement was performed on a FACSCalibur (Becton Dickinson, Heidelberg, Germany), as mentioned above. Propidium iodide (PI, 0.5 μg/μl; Sigma-Aldrich, Schnelldorf, Germany) was added to all cell suspensions immediately before the FACS analysis to exclude dead cells. The data were analyzed using the FlowJo software (Tree Star Inc., Ashland, USA).

[³H]-Thymidine incorporation was assayed as follows: Ltk.wt cells, γ-irradiated with 100 Gy and modified for 1 hr with 100 HU NDV, were used as stimulator cells in 96-well microtiter plates ($1 \times 10^4$ cells/well). Then, the bi- or trispecific fusion proteins and $1 \times 10^5$ purified T cells were added in 50 μl culture medium (RPMI-1640 plus 5% FCS), respectively. After 2 days of incubation at 37° C. in a 5% CO₂ incubator, 1 μCi [³H]-thymidine (Amersham Biosciences, Freiburg, Germany), diluted in 50 μl RPMI-1640 plus 5% FCS, were added per well for another 18 hr incubation. Incorporation of radioactivity into the DNA was assessed as described (Haas et al., 1999). Mean counts per minute (cpm) were calculated from duplicates. Mean counts per minute (cpm) were calculated from triplicates.

EXAMPLE 2

T Cell Costimulatory Activity of NDV Specific Antibody Fusion Proteins

Purified T cells from peripheral blood were stimulated with NDV infected Ltk fibroblasts as stimulator cells (Ltk. wt-NDV) and a suboptimal pre-tested concentration of bsHN-CD3. Separate groups received in addition either bsF-CD28 or tsF-IL-2-CD28 in decreasing amounts. After co-incubation for two days, radioactive thymidine was added and its uptake into DNA determined 18 hours later. As can be seen from FIG. 3 A, the bispecific protein showed costimulatory activity when applied at 100 units F activity. The trispecific protein showed a stronger costimulatory activity, especially at lower dilutions. The three control lines indicate the thymidine uptake of the T cells when stimulated with virus infected cells in presence of bsHN-CD3 alone, tsF-IL-2-CD28 alone or bsF-CD28 alone. Thus, the anti-CD3 signal alone (1) could be augmented by one costimulus (2a) mediated via anti-CD28 and more effectively by two costimuli (2a and 2b) mediated via anti-CD28 and IL-2.

Figure 3:
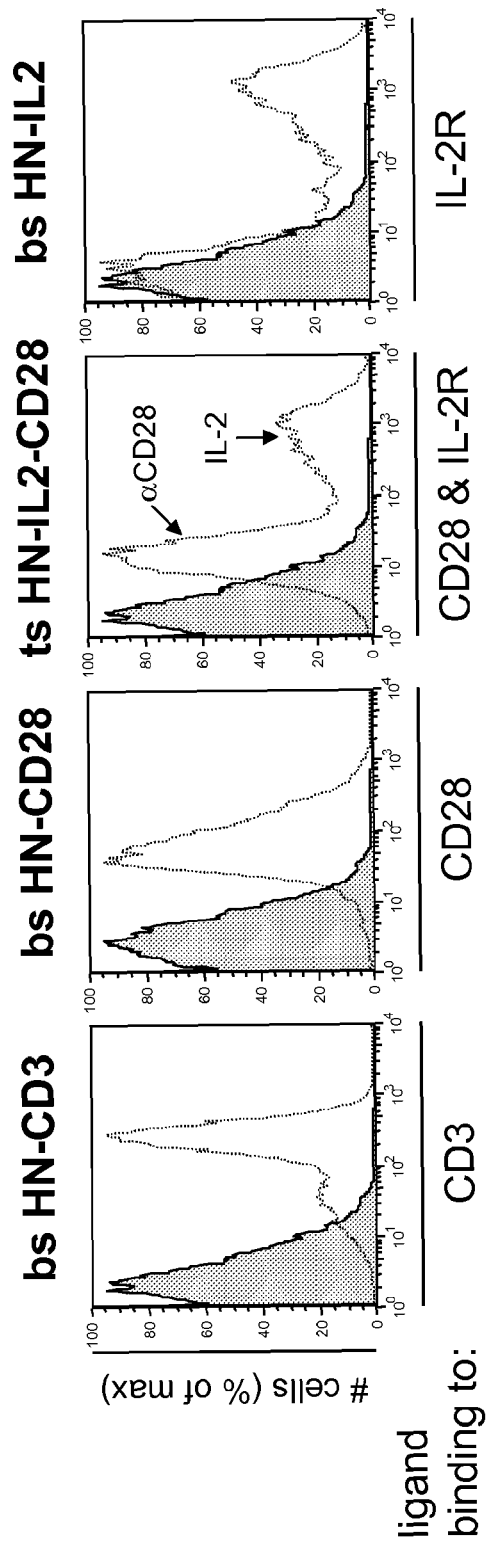
FIG. 3 demonstrates that the bispecific fusion exhibited costimulatory activity for purified T cells when applied at 100 units F activity. The trispecific protein showed a stronger costimulatory activity, especially at higher dilutions. Negative controls included T cells on to top of virus-infected vaccine cells in the pressure of either bsHN CD3 alone (dashed line), of tsF-IL-2-CD28 alone (dotted line), or of bsF-CD28 alone (dashed-dotted line). Thus, the anti-CD3 signal alone (signal 1) could be augmented by one costimulus (signal 2a) mediated via anti-CD28, and more effectively by two costimuli (signals 2a plus 2 b) mediated via anti-CD28 and IL-2 (A). The proportion of dividing cells after 5 or 7 days of stimulation with virus-infected vaccine cells from cultures that received either no additional proteins or the various proteins alone, or in combination is shown in (B).

The results so far have been obtained with purified T cells from the peripheral blood of normal healthy donors. Since these T cells contain memory and naïve T cells and since the activation requirements of naïve T cells are more complex than those of memory T cells, it was decided to study the activation of purified naïve T cells by a vaccine modified with the various fusion proteins. Human peripheral blood mononuclear cells (PBMC) were isolated via Ficoll-Paque (Amersham Biosciences, Freiburg, Germany) centrifugation from buffy coat or from fresh heparanized blood of healthy donors. Untouched T cells (TC) were purified with the T Cell Negative Isolation Kit (Dynal, Hamburg, Germany), which is based on the magnetic separation of the non-T cells by labelling them with mouse mAbs directed against human CD14, CD16a/b, CD56 and HLA-II DR/DP, and by subsequently removing them with the use of Dynabeads coated with an Fc-specific human IgG4 against mouse IgG. The isolation of naïve T cells (nTC) consisted in adding an anti-CD45RO antibody (BD Pharmingen, Heidelberg, Germany) to the above mentioned antibody cocktail, in order to remove the memory T cell fraction. The purification procedure included the removal of T reg cells which was confirmed by FACS analysis. The highly pure naïve T cells were labelled with CFSE in order to be able to quantify later the numbers of cell divisions by FACS analysis. FIG. 3 B shows the proportion of dividing cells after 5 or 7 days of stimulation with virus infected vaccine cells from cultures that received either no additional proteins or the various proteins alone or in combination. While the majority of T cells in the controls stimulated with either suboptimal signal 1 alone or signal 2a or 2 b alone or 2 a+2 b alone underwent no divisions, the majority of cells that were provided with signal 1 in combination with signal 2a, 2 b or 2 a+2 b underwent 1, 2 or even 3 cell divisions. It is interesting to notice from these quantitative data that the vaccine bound virus specific proteins in combination could activate naïve T cells and that the immunocytokine (signal 2b) was at least as effective in this assay as the bispecific antibody (signal 2a).

EXAMPLE 3

Induction of T Cell Activation Markers and Effector Function in Naïve Human T Cells by the Antibody Fusion Protein While in the previous experiments a virus-infected Ltk fibroblasts was used as vaccine stimulator cells, in the following experiments Ltk cells stably transfected with the viral HN gene (Ltk. HN.A2 cells) are used. Such cells have a more homogenous HN expression although the density of HN molecules at the cell surface is lower than on virus infected cells. $1 \times 10^5$ purified naïve T cells were stimulated with $1 \times 10^4$ irradiated Ltk. HN.A2 cells together with HN-specific fusion proteins either alone or in combination. Six days later we followed the upregulation of CD25, the α-chain of the IL-2 receptor, and CD45 RO, a marker for the transition of naïve to memory cells. Before it was observed that the upregulation of these two markers is very similar and occurs with similar kinetics in particular on proliferating T cells. The results of this investigation show that the classical combination of anti-CD3 in a suboptimal dose with anti-CD28 at an optimal concentration of about 40 units induces an upregulation of both markers in 20% of the T cells. The new antibody fusion proteins containing IL-2 induced a much stronger co-stimulatory effect so that at least twice as many T cells expressed these two markers in comparison to bsHN-CD28. The superior co-stimulatory activity was observed at all doses of co-stimulus. The reduced co-stimulatory activity observed at the highest concentration is possibly due to competition with the bsHN-CD3 reagent that has to provide signal 1. To see whether the antibody fusion proteins (sometimes also referred to as immunocytokines) could also activate effector functions in T cells it was decided to study on activated naïve CD8 T cells the upregulation of CD107 a, a lysosomal associated membrane protein which becomes expressed at the outside of the plasma membrane when CD8 T cells exert cytotoxic function. The results showed a dose dependent upregulation on activated CD8 T cells (CD8 CD25 double positive cells) of CD107 a. At the optimal amount of co-stimulus (40.5 U) only about 40% of the cells that received the anti-CD28 costimulus became cytotoxic while about 80% were cytotoxic after co-stimulation with the new IL-2 immunocytokines. It was conclude that IL-2 targeted to a virus antigen on a vaccine stimulator cell via immunocytokines introduces T cell co-stimulatory activity. The CSFE-labelled naïve T cells which are at the beginning CSFE high, CD25 negative, CD45 RO negative and CD107 a negative, change after activation their phenotype to CFSE low, CD25 positive, CD45 RO positive and CD107 a positive. In such a context IL-2 seems to have a similar costimulatory activity as anti-CD28. The data suggest a synergism between the two costimuli.

CFSE-Based Proliferation of Naïve T Cells was assayed as follows: Ltk.wt cells, γ-irradiated with 100 Gy and modified for 1 hr with 100 HU NDV Ulster 6/92, were used as stimulator cells in 96-well microtiter plates ($1 \times 10^4$ cells/well). The bi- or trispecific fusion proteins were added in 50 μl culture medium (RPMI-1640 plus 5% FCS). As responders, purified naïve T cells were labelled for 10 min at room temperature in PBS with 0.2 μM of the live cell dye carboxyfluorescein diacetate succinimidyl ester (CFSE; Molecular Probes, Leiden, Netherlands). The reaction was quenched by washing the cells thoroughly in culture medium (RPMI-1640 plus 5 FCS). Finally, the cells were added to the wells ($1 \times 10^5$/well). After 5 and 7 days of incubation at 37° C. in a 5% $CO_2$ incubator, the activated naïve T cells were harvested and analyzed by flow cytometry as described above. Only lymphocytes were gated. The number of cell divisions was determined by comparing the CFSE dilution in comparison to the negative control (0 divisions). For virus infection, the avirulent, non-lytic strain Ulster of NDV (Batch 6/92) was used. Origin, maintenance, purification and quantification have been described previously (Schirrmacher 1999, Gene Ther 6, 63-73).

EXAMPLE 4

Bystander Anti Tumor Activity Induced by the Antibody Fusion Proteins

Having optimized the requirements for activation of naïve T cells by a tumor vaccine (i.e. the antibody fusion protein) next it was decided to evaluate the activation of bystander anti tumor activity. For this purpose we have recently established the tumor-neutralization assay (TNA) which is basically a mixed lymphocyte tumor cell culture (MLTC) performed on top of an adherent tumor cell monolayer as bystander target.

Mixed Lymphocyte Tumor Cell Culture (MLTC) was carried out as follows: $1\times10^5$ freshly isolated naïve T cells per well were co-incubated in 96-well round bottom microtiter plates with $1\times10^4$ stimulator cells per well (i.e. responder to stimulator cell ratio 10:1). As stimulator (vaccine) cells, we used either murine Ltk.wt or human MCF-7 cells that were inactivated with 100 or 200 Gy γ-irradiation, respectively, via a $^{137}$Cs source (Gammacell 1000, Atomic Energy of Canada, Chalk River, Canada) and then infected with NDV Ulster (100 HU per $1\times10^7$ cells) as described (Schirrmacher et al., 1999). After the indicated durations of incubation in presence or absence of the fusion proteins in the corresponding culture medium, the cells were harvested, washed and either used in the TNA assay (described below) of stained for FACS analysis.

For the TNA assay system, experimental tests were performed in triplicates in 96-well round-bottom microtiter plates. For effector cell passages, the setup was scaled up to a E-well TNA system (in duplicates). Briefly, in a 96- or 6-well plate, $3\times10^3$ or $5\times10^4$ live MCF-7 monolayer tumor cells, respectively, were added to the wells in culture medium for 4 hr until they became adherent. Effector cells were either freshly isolated, non-activated PBMC or purified T cells from healthy donors or naïve T cells that had been pre-activated in an MLTC. The effector cells were added to the wells at an effector to tumor cell ratio of 5:1 (i.e. $1.5\times10^4$ cells/well for the 96-well TNA and $2.5\times10^5$ cells/well for the 6-well TNA). When using fresh (i.e. non-activated) effector cells, $1\times10^3$ or $1.67\times10^4$ MCF-7-NDV vaccine cells (see MLTC) for the 96- or 6-well TNA, respectively, as well as the indicated amounts of the fusion proteins had to be added. The final volumes were 200 µl for the 96-well TNA and 3 ml for the 6-well TNA. The plates were then wrapped in cling film to prevent evaporation and incubated at 37° C. in a 5% $CO_2$ incubator, until the tumor monolayer in the control wells was confluent (6-7 days for the first passage and 3 days for the following passages or for MLTC pre-activated cells). At the end of the assay, the supernatants of the 96-well TNAs were removed, the wells carefully washed 5 times with 200 µl RPMI-1640 medium (plus 5 FCS) to remove non-adherent cells. After the last wash, the wells were filled with 100 µl RPMI-1640 medium (plus 5% FCS), before 20 µl MTS solution (MTS Cell Titer 96® $AQ_{ueous}$; Promega, Mannheim, Germany) was added. The plates were then incubated for 45 min at 37° C. in the dark. When in the control monolayer wells the colour switched from yellow to brown, the reaction was stopped by adding 20 µl 10% SDS per well. The plates were then evaluated in an ELISA reader at 490 nm. The background was taken from 3 control wells containing only medium, MTS reagent and SDS solution. The percent tumor growth inhibition was calculated according to:

$$\text{tumor growth inhibition}[\%] = \left(1 - \frac{A_{490}\ \text{experimental well} - A_{490}\ \text{background}}{A_{490}\ \text{positive control} - A_{490}\ \text{background}}\right) \times 100$$

For passages, the effector cells from the 6-well plates were carefully harvested, washed twice in PBS, resuspended in culture medium and distributed onto fresh MCF-7 monolayer target cells ($2.5\times10^4$ cells/well or $4.2\times10^5$ cells/well for 96- or 6-well TNA, respectively).

Figure 4:
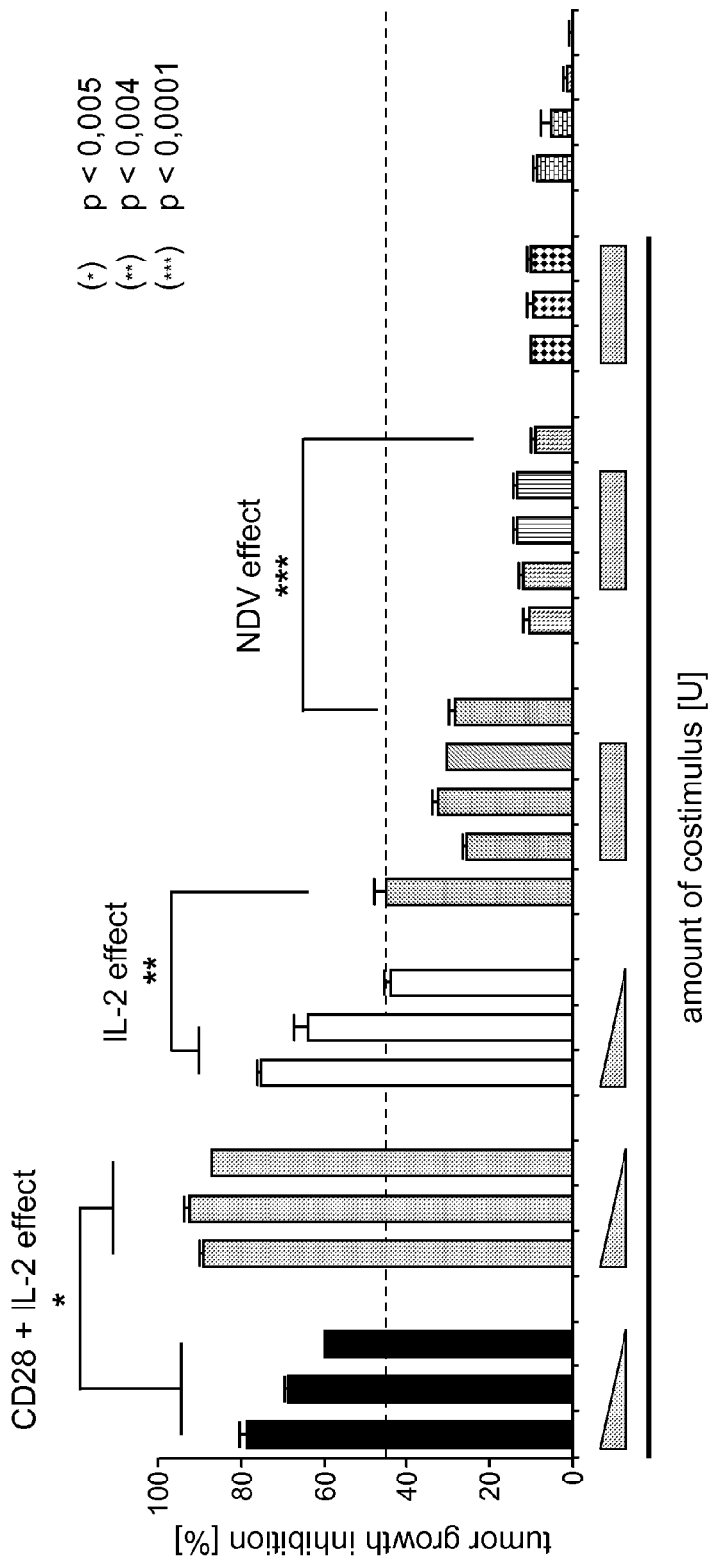
FIG. 4 shows representative results of such a TNA assay. The x-axis indicates the amount of costimulus which has been titrated. In control cultures only the results obtained with the maximum of costimulus is shown. A significantly augmented bystander tumor growth inhibition can be seen when the suboptimal anti-CD3 signal is combined with an IL-2-mediated signal. The combination of an IL-2-mediated signal with a CD28-mediated signal gives a further augmentation of bystander antitumor activity resulting in an almost complete tumor monolayer destruction (A). Since the direct TNA assay includes the steps of T cell activation and effector function, it was decided to test separately the effector function. The results are shown (B). There was a significantly higher effector activity in cultures in which the costimulus was provided by IL-2 or IL-2 plus anti-CD28 in comparison to anti-CD28 alone. (C) shows that in the latter situation of T cell activation, a longer lasting antitumor activity was induced than in T cells activated only via anti-CD3 plus anti-CD28.
Figure 4:
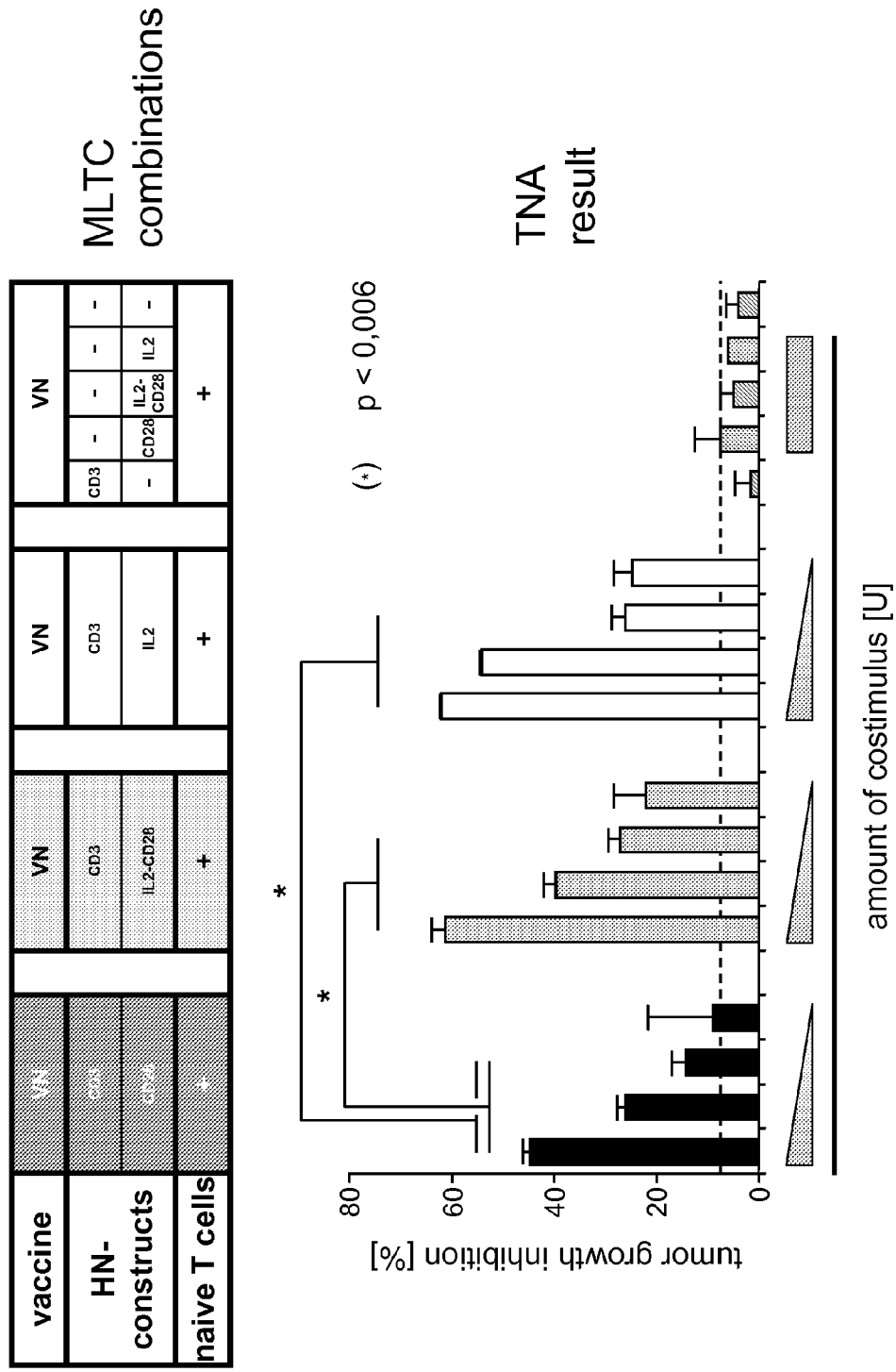
Figure 4:
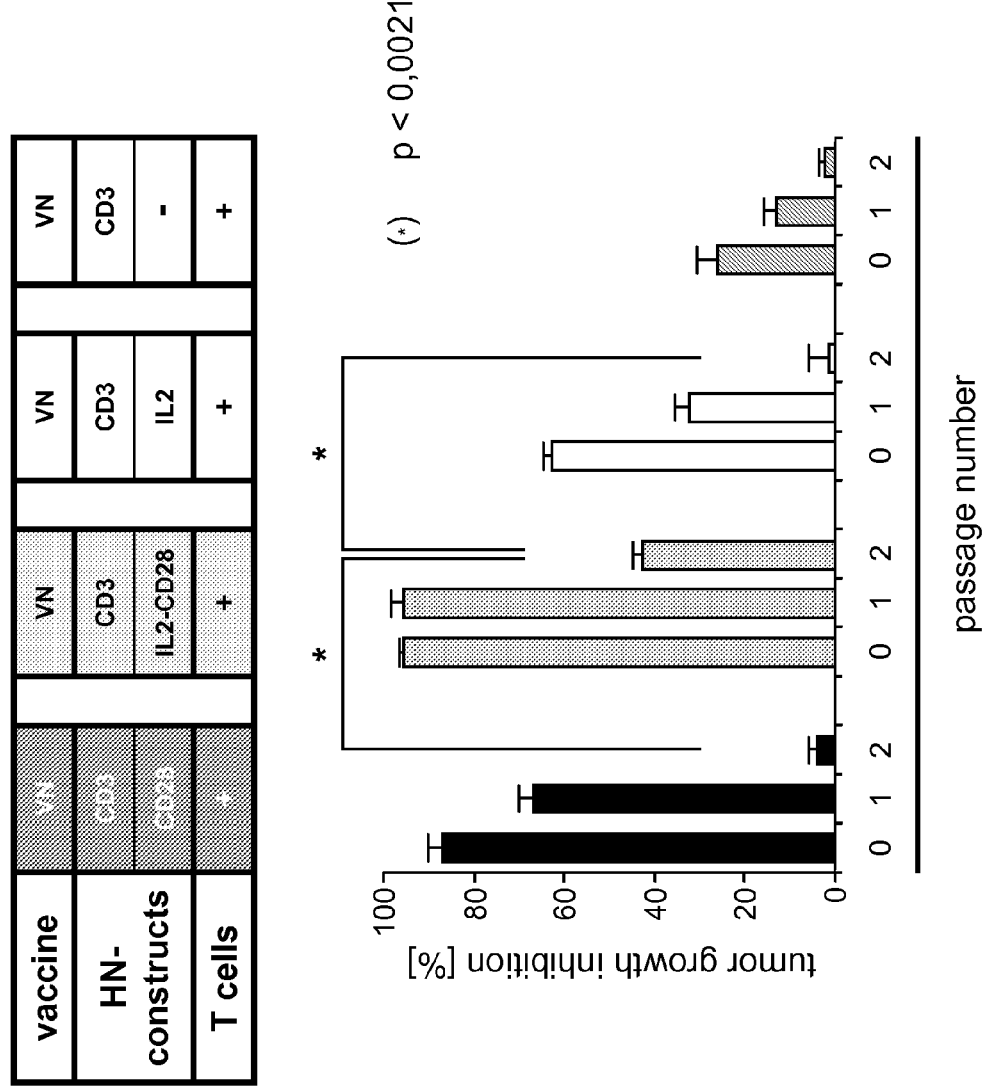
Figure 5:
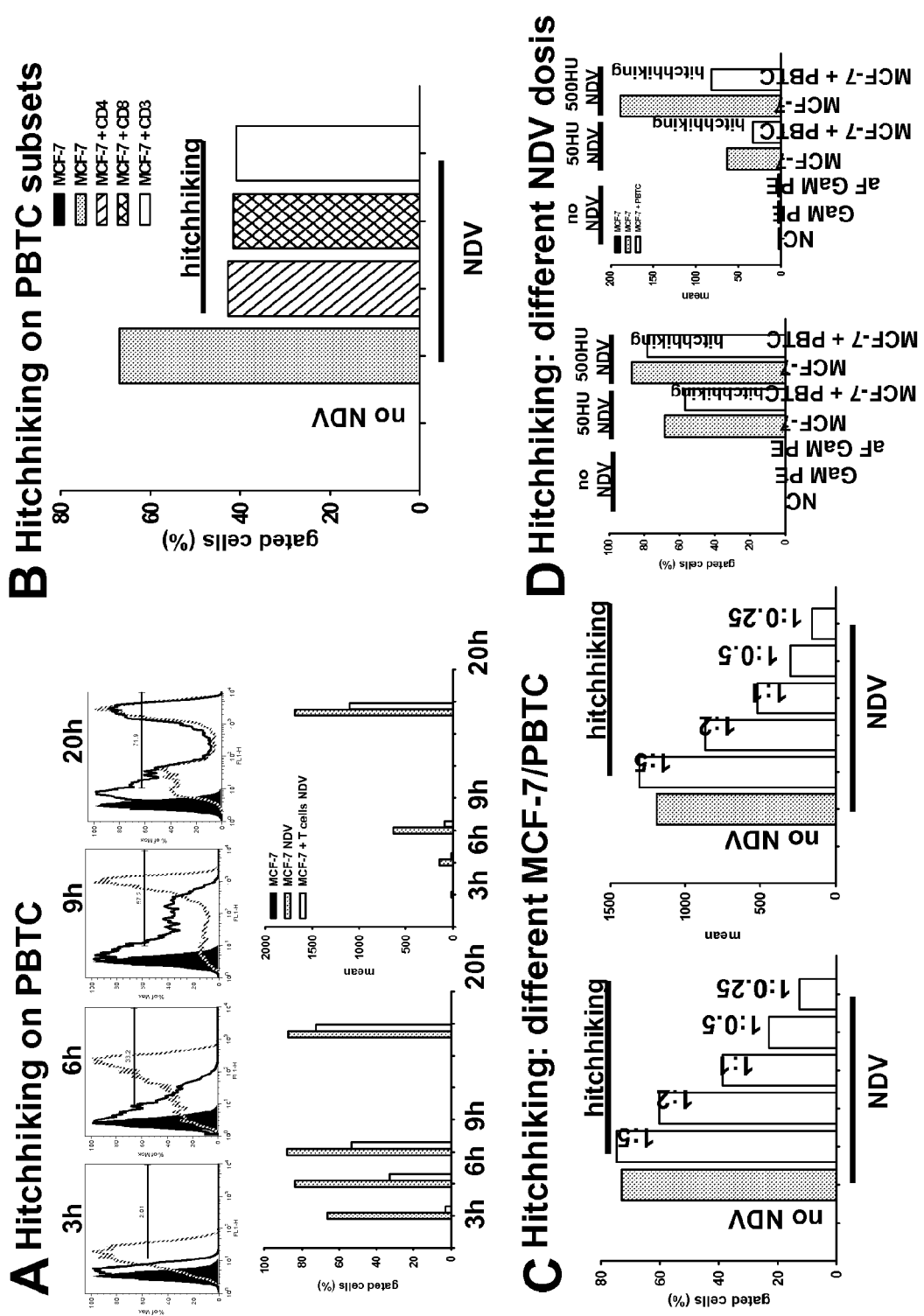
FIG. 5 shows evidence for transfer of NDV from infected peripheral blood derived T cells (PBTC) to tumor cells (human MCF-7 breast carcinoma cells) in vitro. A Kinetics of the hitchhiking phenomenon. Tumor cells were either directly infected by recombinant NDV with incorporated EGFP gene (NDFL-EGFP; 50 HU per 10 million cells) or they were co-incubated with NDV-infected human T cells (tumor cell to T cell ratio 1:5). 3 to 20 hours later the fluorescent EGFP signal in tumor cells was quantified by FACs analysis. The upper curves show the histograms, the lower curves the percentage of infected tumor cells. Thus, co-incubation with infected T cells allows the virus to transfer to tumor cells and to infect these. The virus which is first adsorbed to the T cells can be released upon contact with tumor cells. The infection of tumor cells via hitchhiking is delayed in comparison to direct infection. B Comparison of T cell subsets for hitchhiking capacity. The experimental set-up was as in A. Human T cells from blood were purified by beads into total T cells (CD3), helper T cells (CD4) or cytotoxic T cells (CD8). All T cells transfer the virus to tumor cells with a similar capacity. C Virus hitchhiking in dependency of the ratio of tumor cells to T cells. The ratio 1:5 gives the best results, both in terms of percent infected gated tumor cells (left) or in terms of mean fluorescence intensity (right). D Virus hitchhiking in dependency of virus dose. The higher dose (500 HU per 10 million T cells) gives a higher effect. In this experiment NDV Ulster was used and the virus antigen expressed on infected tumor cells was measured after staining the cells with a mouse anti NDV F monoclonal antibody followed by PE labelled goat anti-mouse Ig reagent (GaM).

Co-incubation for 5-7 days with the vaccine cells modified by virus infection and addition of fusion proteins mediating signal 1 and co-stimuli, results in the generation of cytotoxic effector function of the T cells and in the release of a variety of cytokines. During this effector phase the bystander tumor cells can be lysed or their proliferation can be inhibited. At the end of the assay the amount of surviving tumor cells is measured after removal of the non-adherent cells by addition of MTS, a live cell staining reagent. Representative results of such a TNA assay are shown in FIG. 4 A. The x-axis indicates the amount of costimulus which has been titrated. In control cultures only the results obtained with the maximum of co-stimulus is shown. If read the results from right to left the NDV effect can be seen, namely the significantly increased % of tumor growth inhibition in all cultures in which the tumor vaccine was virus-infected. A significantly augmented bystander tumor growth inhibition can be seen when the suboptimal anti-CD3 signal is combined with an IL-2 mediated signal. Differences between two means were calculated in Excel software with the Student's t-test and were regarded as significantly different when the p-value was <0.05. The combination of an IL-2 mediated signal with a CD28 mediated signal gives a further augmentation of bystander antitumor activity resulting in an almost complete tumor monolayer destruction. Since this direct TNA assay includes the steps of T cell activation and effector function it was decided to test separately the effector function. The results are shown in FIG. 4 B. MLTC cultures were first performed in the absence of tumor monolayers for 6 days with Ltk HN.A2 vaccine cells and the indicated HN constructs. Upon transfer to MCF-7 human breast carcinoma cells, the generated effector T cells exerted within 3 days the indicated tumor growth inhibition. There was a significantly higher effector activity in cultures in which the co-stimulus was provided by IL-2 or IL-2 and anti CD28 in comparison to anti CD28 alone. FIG. 4 C shows that in the latter situation of T cell activation, a longer lasting antitumor activity was induced than in T cells activated only via anti-CD3 and anti-CD28. Repeated transfer of MLTC activated cells (P0) on day 6 (P1) and day 9 (P2) onto fresh MCF-7 tumor monolayers revealed that T cells co-stimulated via tsHN-IL-2-CD28 exerted in P1 and P2 20-40% higher bystander tumor growth inhibition potential.

The invention claimed is:

1. An antibody fusion protein comprising:

an antigen binding domain of an antibody that specifically recognizes hemagglutinin-neuromimidase (HN) or F surface antigen (F) of New Castle Disease Virus (NDV), and (ii) an antigen binding domain of an antibody that specifically recognizes human CD28, and (iii) a human interleukin-2 (IL-2), wherein the IL-2 is between the antigen binding domain of (i) and the antigen binding domain of (ii) in the antibody fusion protein.

2. A method of stimulating T cells by providing costimulatory signals to said T cells comprising administering to a human subject the antibody fusion protein according to claim 1.

* * * * *

UNITED STATES PATENT AND TRADEMARK OFFICE
CERTIFICATE OF CORRECTION

| | |
|---|---|
| PATENT NO. | : 8,142,791 B2 |
| APPLICATION NO. | : 12/516530 |
| DATED | : March 27, 2012 |
| INVENTOR(S) | : Volker Schirrmacher et al. |

It is certified that error appears in the above-identified patent and that said Letters Patent is hereby corrected as shown below:

ON THE TITLE PAGE:

At item (86), change the § 371(c)(1), (2), (4) Date from "May 27, 2009" to --Jul. 30, 2009--.

Signed and Sealed this
Twenty-fourth Day of July, 2012

David J. Kappos
*Director of the United States Patent and Trademark Office*